United States Patent [19]

Yamamizu et al.

[11] Patent Number: 4,599,175
[45] Date of Patent: Jul. 8, 1986

[54] PROCESS FOR SEPARATING AND PURIFYING METALLIC ELEMENTS BY DISPLACEMENT CHROMATOGRAPHY

[75] Inventors: Takafumi Yamamizu, Yokohama; Fumiaki Kawakami, Hyuga, both of Japan

[73] Assignee: Asahi Kasei Kogyo Kabushiki Kaisha, Osaka, Japan

[21] Appl. No.: 651,850

[22] Filed: Sep. 18, 1984

[30] Foreign Application Priority Data

Sep. 30, 1983 [JP] Japan .................................. 58-180619

[51] Int. Cl.$^4$ ............................................. B01D 15/08
[52] U.S. Cl. ..................................... 210/635; 210/656
[58] Field of Search ....................... 210/635, 636, 198.2

[56] References Cited

U.S. PATENT DOCUMENTS

| | | | |
|---|---|---|---|
| 3,228,750 | 1/1966 | Lindstrom et al. | 210/635 |
| 3,484,390 | 12/1969 | Bauman et al. | 210/656 |
| 3,891,413 | 6/1975 | Sievers | 210/656 |
| 4,394,353 | 7/1983 | Miyake et al. | 210/674 |
| 4,411,793 | 10/1983 | Kato | 210/656 |
| 4,431,546 | 2/1984 | Hughes | 210/656 |

FOREIGN PATENT DOCUMENTS 50-80387  6/1975 Japan .
52-45647 11/1977 Japan .

OTHER PUBLICATIONS

Anwendung Chelatbildender Ionenaustauscherharze in der Analytischen Chemie by R. Hering in Zeitschrift fur Chemie 5, 402–409, (1965).
Extraction Chromatography with Macroreticular Polymer Beads Impregnated with Monothiodibenzoylmethane Solution by Sugil et al., Talanta, vol. 29, No. 8, Aug. 1982, pp. 697 to 699.

Primary Examiner—John Adee
Attorney, Agent, or Firm—Birch, Stewart, Kolasch & Birch

[57] ABSTRACT

By the displacement chromatographic process comprising passing a solution containing a plurality of metallic elements to be separated through a column packed with activated chelating resin, passing an eluent through the column and collecting successive portions of the resultant eluate, the metallic elements can be separated into individual metallic elements not only in a high state of purity but also in a high state of concentration, with a greatly improved column efficiency.

15 Claims, No Drawings

PROCESS FOR SEPARATING AND PURIFYING METALLIC ELEMENTS BY DISPLACEMENT CHROMATOGRAPHY

This invention relates to a process for separating and purifying metallic elements by displacement chromatography. More particularly, the present invention is concerned with a process which comprises passing a solution containing a plurality of metallic elements to be separated through a column packed with an activated chelating resin to adsorb the elements on the resin, passing an eluent through the column to form individual metallic elements into bands, further passing an eluent through the column, and collecting successive portions of the resultant eluate.

The demand for pure metallic elements, especially pure rare earth elements, is rapidly increasing in accordance with the recent rapid advance of technologies relating to semiconductors, fluorescent substances, glass materials, alloys and the like in the field of industrial electronics. Hence, a process for effectively separating and purifying a metallic element has been desired. As one of the processes for obtaining a pure metallic element to be used in the above-stated technologies, a solvent extraction method is known which is employed for the separation and purification of a metallic element on a commercial scale. The solvent extraction method is disadvantageous in that it is accompanied by loss of the extractant and inclusion of the extractant in the desired product. With respect to the solvent extraction method, reference may be made to J. Korkisch: "Modern Methods for the Separation of Rare Metal Ions," Pergamon Press, Oxford, 1969.

Moreover, a method for separating rare earth elements is known in which an ion exchange resin is used in combination with a chelating agent. In such a method, it is required that a chelating agent such as ethylenediaminetetraacetic acid (EDTA) and citric acid be added to the liquid phase. Hence, this method has a drawback in that a chelating agent is included in the separated metallic element. The inclusion of a chelating agent in the separated metallic element causes employment of the metallic element to be unfeasible in important fields such as those which utilize highly pure fluorescent substances and other materials. When such a method is still intended to be utilized, it becomes disadvantageously necessary to implement an additional step for removing the chelating agent. Further, the solubility of a chelating agent in an acid liquid phase is generally low. This sets an upper limit under which the concentration of metal ions in the solution must be controlled. Hence, in this method, separation of metal ions is possible at low concentrations only. Therefore, this method is disadvantageous from the viewpoint of commercial production. With respect to the above-described method in which an ion exchange resin is used in combination with a chelating agent, reference may be made to U.S. Pat. Nos. 2 798 798, 2 549 582, 3 228 750, and Japanese Patent Application Publication No. 52-45647/1977.

In view of the current situation as described above, the present inventors have made intensive investigations to develop an advantageous process for effectively separating and purifying metallic elements. For realizing such a process, the present inventors have particularly tried to use various kinds of resins without using a chelating agent, such as EDTA, which causes one of the most serious disadvantages in the conventional methods. As a result, the present inventors have found that the above-metioned disadvantages of the conventional methods can be obviated by a process in which displacement chromatography is conducted using a chelating resin as a packing material for a column. Also, the present inventors have found that, by such a novel process, a mixture of rare earth elements which is usually very difficult to separate because of the great chemical similarity therebetween can be separated into individual species not only in a high state of purity but also in a high state of concentration, and that a greatly improved column efficiency can be achieved. The present invention has been completed based on such novel findings.

Accordingly, it is an object of the present invention to provide a process for the separation of metallic elements by displacement chromatography by which a plurality of metallic elements can be separated into individual species not only in a high state of purity but also in a high state of concentration and a greatly improved column efficiency can be achieved. The foregoing and other objects, features and advantages of the present invention will be apparent to those skilled in the art from the following detailed descriptions and appended claims.

According to the present invention, there is provided a process for separating and purifying metallic elements by displacement chromatography, which comprises the steps of:

(1) in either order,
  (a) packing a column with a chelating resin; and
  (b) treating the chelating resin with a regenerative solution containing an activator,
to obtain a column of an activated chelating resin;

(2) passing through the column of the activated chelating resin a solution containing a plurality of metallic elements to be separated to adsorb the elements on the activated chelating resin, thereby forming an adsorption band of the metallic elements in the column packed with the activated chelating resin;

(3) passing an eluent through the column of the resin having the adsorption band of the metallic elements to form bands of the individual metallic elements;

(4) further passing an eluent through the column, causing the bands of the individual metallic elements to pass down the column; and (5) collecting successive portions of the resultant eluate.

The metallic elements which may be advantageously separated according to the process of the present invention are ordinary metallic elements and amphoteric elements having a capacity of being adsorbed on the chelating resin. As specific examples of the metallic elements which can be separated by the process of the present invention, there may be mentioned elements belonging to Group III A, Group IV A, Group V A, Group VIII and Group III B (including scandium, yttrium and lanthanide elements) of the long period periodic table. The present invention is particularly advantageous for the separation of rare earth elements which has conventionally encountered great difficulties.

The term "rare earth elements" as used in the present invention include the lanthanide elements, i.e., lanthanum, cerium, praseodymium, neodymium, promethium, samarium, europium, gadolinium, terbium, dysprosium, holminum, erbium, thulium, ytterbium and lutecium; and scandium and yttrium.

The "regenerative solution" as is used herein and is a terminology often used in the art means a solution to be used for rendering a chelating resin in an activated form.

The term "activator" as used in the present invention means a material having an adsorbability to the chelating resin smaller than those of metallic elements intended to be separated. The activator which has been adsorbed on the chelating resin can, in turn, be readily displaced by the metallic elements to be separated when the former is contacted with the latter. Specific examples of the activator will be given later. The term "eluent" as used herein means a solution prepaed by dissolving an eluting agent in a solvent including water and an organic solvent. The term "eluting agent" as used herein means a material having an adsorbability to the chelating resin higher than those of the metallic elements intended to be separated. The eluting agent can readily displace the adsorbed metallic elements to render them free when it is contacted therewith. Specific examples of the eluting agent will be given later.

Metallic elements to be separated in the present invention each may be employed in the form of a single kind of salt thereof, such as a salt of $Cl^-$, $SO_4^{2-}$, $NO_3^-$ or $ClO_4^-$ or a mixture thereof. Any other salts than the above-mentioned may be employed insofar as they are soluble in water.

The suitable activator and the suitable eluting agent may be chosen by measuring an adsorption selectivity coefficient defined as:

$$K_B{}^A = \frac{\left[\begin{array}{c}\text{concentration of } A \\ \text{in adsorbent}\end{array}\right]\left[\begin{array}{c}\text{concentration of } B \\ \text{in liquid phase}\end{array}\right]}{\left[\begin{array}{c}\text{concentration of } A \\ \text{in liquid phase}\end{array}\right]\left[\begin{array}{c}\text{concentration of } B \\ \text{in adsorbent}\end{array}\right]}$$

in which $K_B{}^A$ represents an adsorption selectivity coefficient of A against B, A represents an activator or eluting agent, and B represents a metallic element to be separated.

To measure an adsorption selectivity coefficient, a small column such as one having a length of about 30 cm is employed, and the concentrations of an activator, a metallic element and an eluting agent are measured according to customary analytical methods which are useful to measure ion concentrations. A suitable activator is one having a value of $K_B{}^A$, in which A represents the activator and B represents a metallic element to be separated, smaller than 1.0. On the other hand, a suitable eluting agent is one having a value of $K_B{}^A$, in which A represents the eluting agent and B represents a metallic element to be separated, greater than 1.0.

The chelating resin to be used in the present invention is a spherical or fragmental resin having a functional group (hereinafter referred to as "chelating group") which forms a chelate structure with the intended metallic elements. The chelating resin may be porous or may not be porous.

The suitable chelating group is, for example, a member selected from those containing polyaminocarboxylic acid groups, oxime groups, oxine groups and the like. Of them, chelating groups containing polyamino- carboxylic acid groups are preferable. The preferable chelating groups containing polyaminocarboxylic acid groups may have a structure derived from a compound of the below-indicated formula (I) through the removal of hydrogen therefrom or derived from its derivative with a hydrocarbon residue substituent through the removal of a hydrogen therefrom:

in which $R^1$, $R^2$ and $R^3$ each independently represent a hydrogen atom or a group of the formula:

in which $R^5$ represents a hydrogen atom, a metal atom or a hydrocarbon residue having 1 to 4 carbon atoms; $A^1$, $A^2$ and $A^3$ each independently represent a group of the formula:

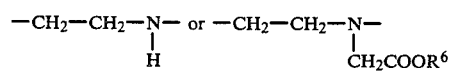

in which $R^6$ has the same meaning as that of $R^5$; and i, j and k each independently are an integer of 0 to 3; provided that the compound of formula (I) has at least one group of the formula:

in which $R^5$ is as defined above.

The more preferable chelating groups are as illustrated below:

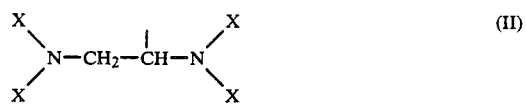

in which X represents a hydrogen atom or a group of the formula:

in which M represents a metal atom or a hydrogen atom,

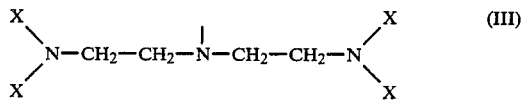

in which X represents a hydrogen atom or a group of the formula:

in which M represents a metal atom or a hydrogen atom, and

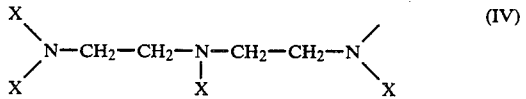

in which X represents a hydrogen atom or a group of the formula:

—CH₂COOM in which M represents a metal atom or a hydrogen atom.

Specific examples of the compound of the above formula (I) include iminodiacetic acid and substituted iminodiacetic acids such as N-methyliminodiacetic acid, N-cyclohexyliminodiacetic acid and N-phenyliminodiacetic acid; polyaminocarboxylic acid having a nitrogen atom such as nitrilotriacetic acid; polyaminocarboxylic acids having two nitrogen atoms such as ethylenediamine-N,N,N',N'-tetraacetic acid, 1,2-propylenediamine-N,N,N',N'-tetraacetic acid, 1-phenylethylenediamine-N,N,N',N'-tetraacetic acid and cyclohexyldiamine-N,N,N',N'-tetraacetic acid; and polyaminocarboxylic acids having three or more nitrogen atoms such as diethylenetriamine-N,N,N',N'',N''-pentaacetic acid, diethylenetriamine-N,N,N'',N''-tetraacetic acid of the formula

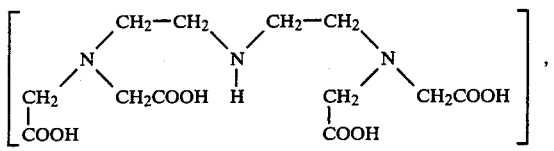

diethylenetriamine-N,N',N'',N''-tetraacetic acid of the formula

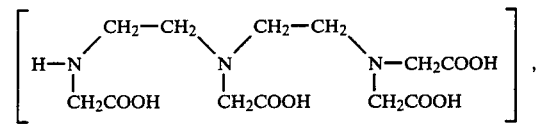

triethylenetetramine-N,N,N',N'',N''',N''',N''''-hexacetic acid and substituted derivatives of the above compounds, and polyethyleneimine substituted with acetic acid groups. Furthermore, polyaminocarboxylic acids such as N-hydroxyethylenediamine-N,N',N'-triacetic acid, 1,3-diaminopropane-N,N,N',N'-tetraacetic acid, 1,4-diaminobutane-N,N,N',N'-tetraacetic acid and the like are also usable in the present invention. Of these polyaminocarboxylic acids, iminodiacetic acid, ethylenediaminetetraacetic acid, diethylenetriamine-N,N,N'',N''-tetraacetic acid, diethylenetriamine-N,N',N'',N'''-tetraacetic acid and their substituted derivatives are more preferable.

The above-mentioned chelating compounds are contained in the chelating resin in the form of a pendant group which is derived by removing a hydrogen atom therefrom.

As the matrix resin of a chelating resin to be employed in the present invention, there may be mentioned natural polymeric substances, or synthetic polymers obtained, with respect to the reaction scheme, by subjecting a single kind or plural kinds of polymerizable monomers to an addition polymerization, a condensation polymerization, an addition condensation polymerization, a polyaddition polymerization or a ring-opening polymerization. With respect to the apparatus, such polymerization may be performed by a suspension polymerization method or a bulk polymerization method. It is required that the matrix resin be insoluble in media for chromatography which are used in the process of the present invention. For example, there may be employed customary matrix resins for chelating resin, such as those of unsubstituted or substituted styrenedivinylbenzene copolymers and the like. It is preferred that the matrix resin of the chelating resin be composed of a crosslinked copolymer from vinyl monomers and crosslinkable monomers. The degree of crosslinking as defined below is not critical, but is preferably in the range of 2 to 80%.

Degree of crosslinking = $\dfrac{\text{Weight of crosslinkable monomer}}{\text{Total weight of crosslinkable monomer and other monomers for preparing crosslinked polymer}} \times 100$ In the process of the present invention, a matrix resin having a structure in which various substituent groups are introduced to a styrene-divinylbenzene copolymer may be preferably employed.

The monomers which may be employed in preparing the matrix resin of the chelating resin to be employed in the present invention include styrene and styrene derivatives such as methylstyrene, ethylstyrene, vinylnaphthalene, 3,4,6-trimethylstyrene, chlorostyrene, methoxystyrene, N,N-dimethylaminostyrene, nitrostyrene, chloromethylstyrene, trifluorostyrene, trifluoromethylstyrene P-(1,2-dibromoethyl)styrene, m-(1,2-dibromoethyl)styrene, P-(diaminoethylaminoethyl)styrene, m-(diaminoethylaminoethyl)styrene and aminostyrene; butadiene; acrylonitrile derivatives; acrylic acid and acrylic esters such as methyl acrylate and chloromethyl acrylate; methacrylic acid and methacrylic esters such as cyclohexyl methacrylate, dimethylaminoethyl methacrylate, glycidyl methacrylate and methyl methacrylate; diethyl maleate; diethyl fumarate; vinylketones such as methyl vinyl ketone and ethyl vinyl ketone; vinylidenes; acrylamide derivatives; aliphatic acid vinyl esters such as vinyl acetate, vinyl butylate and vinyl caprate; epoxybutadiene; and sulfur-containing compounds such as vinylsulfonic acid ethyl ester, vinylsulfonic acid phenyl ester styrenesulfonic acid, styrenesulfonates, styrenesulfonic acid butyl ester, and methylvinyl sulfide.

The crosslinkable monomers which may be employed in preparing the matrix resin of the chelating resin to be employed in the present invention include divinylbenzene, divinyltoluene, divinylnaphthalene, divinylethylbenzene, trivinylbenzene, divinyldiphenylmethane, divinylbenzyl, divinylsulfone, divinylketone, bis(vinylpyridinoethyl)ethylenediamine, diallyl phthalate, triallylamine, N,N'-ethylenediacrylamide, ethylene glycol dimethacrylate, triethylene glycol dimethacrylate, trimethylpropane triacrylate, triallyl isocyanurate and diallyl melamine.

As described, preferred methods of producing particles of the matrix resin may be a customary suspension polymerization method or a method in which bulk polymerization is effected, followed by pulverization. With respect to the customary suspension polymerization, in conducting the addition polymerization, condensation polymerization or the like of oil-soluble monomers, an oil-in-water suspension may be employed, and in conducting the addition polymerization, condensation polymerization or the like of water-soluble monomers, a water-in-oil suspension may be employed with addition of various agents for stabilizing the suspension.

In the case of using oil-soluble monomers, the suspension may preferably contain a viscous substance such as gum arabic, gamboge, rosin, pectin, alginate, tragacanth gum, agar, methyl cellulose, starch carboxymethyl cellulose, karaya gum, and gelatin; a synthetic high molecular weight substance such as sodium polyacrylate, polyvinyl alcohol, polyvinyl pyrrolidone and diacetoolein; and an inorganic substance such as magnesium aluminum silicate, hydrated magnesium silicate, titanium oxide, zinc oxide, calcium carbonate, talc, barium sulfate, calcium phosphate, aluminum hydroxide and silicic acid anhydride, and, if necessary, the suspension may preferably contain a salt such as sodium chloride, a pH controlling agent and an emulsifier. In suspending water in oil, it is preferred to employ a surfactant together with a suspending agent comprising a synthetic high molecular weight substance. Particularly preferable surfactants include sorbitan esters, sorbitan ester ethers, fatty acid soap and fatty acid glycerides.

As the representative structure of a chelating resin to be used in the present invention, there may be mentioned a structure in which repeating units represented by the following formulae V and VI are incorporated into a styrene-divinylbenzene copolymer.

Structural formula (V)

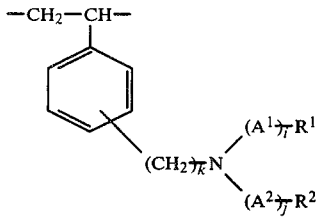

in which $R^1$ and $R^2$ each independently represent a hydrogen atom or a group of the formula:

—$CH_2COOR^5$ in which $R^5$ represents a hydrogen atom, a metal atom or a hydrocarbon residue having 1 to 4 carbon atoms;

$A^1$ and $A^2$ each independently represent a group of the formula:

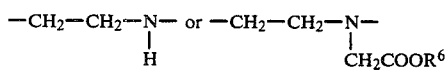

in which $R^6$ has the same meaning as that of $R^5$; and i and j each independently are an integer of 0 to 3, and k is an integer of 1 to 3;

provided that the structural unit of formula (V) has at least one group of the formula:

—$CH_2COOR^5$ in which $R^5$ is as defined above.

Structural formula (VI)

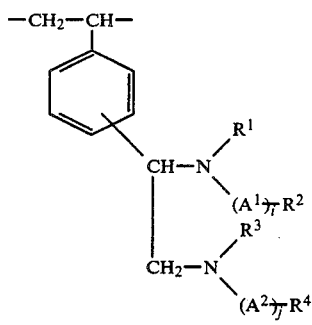

in which $R^1$, $R^2$, $R^3$ and $R^4$ each independently represent:

H or —$CH_2COOR^5$ $A^1$ and $A^2$ each independently represent a group of the formula:

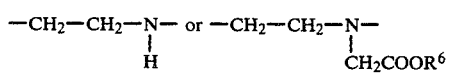

and, i and j each independently are an integer of 0 to 3;

provided that the structural unit of formula (VI) has at least one group of the formula:

—$CH_2COOR^5$.

A chelating resin which contains at least two —$CH_2COOR^5$ groups in the structural unit represented by the formula (V) wherein k=1 or 2 and either i=1 and j=1 or i=0 and j=2 and a chelating resin which contains at least two —$CH_2COOR^5$ groups in the structural unit represented by the formula VI wherein i=j=0 are most preferable.

As the method for the preparation of these chelating resins, in the case of a chelating resin comprising the repeating units represented by the structural formula (V), there may be mentioned, for example, a method in which a copolymer of chloromethylstyrene-divinylbenzene is reacted with an iminodiacetic acid ethyl ester, a method in which a copolymer of chloromethylstyrene-divinylbenzene is reacted with diethylenetriamine and the resulting reaction product is then reacted with a chloroacetic acid, and a method in which a copolymer of p-(diaminoethylaminoethyl)styrene-divinylbenzene is reacted with chloroacetic acid. In the case of a chelating resin comprising the repeating units represented by the formula (VI), there may be mentioned, for example, a method in which a copolymer of (1,2-dibromoethyl)styrene-divinylbenzene is reacted with iminodiacetic acid.

It is preferable that the copper ion adsorbing capacity of the chelating resin to be used in the present invention be 0.5 millimole or more per gram of a dried resin. This is so because if the chelating resin has a copper ion-adsorbing capacity less than 0.5 millimole per gram of a dried resin, separation of elements cannot be performed to a sufficient level. There is no critical limitation with respect to the particle size of a chelating resin. However, it is preferred to employ a chelating resin having a particle size of 5 to 1000 mesh, Tyler (4 to 0.015 mm in diameter), preferably 50 to 600 mesh, Tyler (0.295 to 0.037 mm in diameter). In case a chelating resin having too large a particle size is used, the separation efficiency is lowered, and on the other hand, in case a chelating resin having too small a particle size is used, the pressure drop in the packed column is unfavourably increased. Therefore, the use of a chelating resin which has too large or too small a particle size is not preferred from a practical viewpoint.

According to the present invention, separation of metallic elements is performed by the so-called displacement chromatography, using the above-mentioned chelating resin. Now, the process of the present invention will be explained with reference to a representative example in which rare earth elements are separated and purified. The process comprises the steps of:

(1) packing a chromatography column with a chelating resin;

(2) supplying to the column a regenerative solution containing an activator, thereby causing the resin to be activated (according to need, followed by passing of water)

(3) passing through the column of the activated chelating resin a solution containing a plurality of rare earth elements to be separated to form an adsorption band of rare earth elements in the column packed with the activated chelating resin (in this step, there is formed the adsorption band with its distinct front boundary from the forward activated chelating resin zone);

(4) further passing an eluent through the column of the resin having the adsorption band of the rare earth elements to form the individual rare earth elements into bands, thereby causing the bands of individual rare earth elements to pass down the column (during the passing-down of the column, the front and rear boundaries of an entire band zone constituted by the individual rare earth element bands are kept clear); and (5) collecting successive portions of the resultant eluate from the bottom of the column. Of the collected portions of the eluate, those portions having an intended purity are taken out as a product. According to need, those portions having a purity lower than the intended one may be recycled to the process of the present invention.

Through the above-mentioned steps, separation and purification of two or more kinds of rare earth elements can be performed simultaneously.

The length of the column packed with an adsorbent is not critical, but it may generally be 15 cm to 50 m, preferably 1 to 15 m. Where the length of the column is less than 15 cm, the efficiency of obtaining pure elements is not so good. The upper limit of the length of the column is determined by taking into consideration the pressure resistance of a pump, materials, etc. employed because the use of too long a column packed ith an adsorbent leads to an increase in pressure loss.

As the activator to be used in the process of the present invention, in the case of the separation of rare earth elements, there may be mentioned, for example, metallic ions of the mono-valent alkali metals such as Li, Na, K, Rb and/or Cs, divalent alkaline earth metals such as Be, Mg, Ca and/or Sr and metals such Ag, Fe, Mn and/or Zn, or ammonium ion and various organic ions. The pH of the regenerative solution is not critical, and can be suitably selected depending upon the kind of the activator. For example, where the separation of rare earth elements is intended, it is preferred that the regenerative solution be an aqueous solution containing, as an activator, Li, Na, K, $NH_4$ or a mixture thereof, and having a pH value of 4 or more, preferably a pH value of 7 to 15. The higher the pH value of the solution, the larger the quantity of the rare earth elements adsorbed on a chelating resin and the higher the separation efficiency. Generally, rare earth elements tend to undergo hydrolysis in a solution having such a highly alkaline pH value as mentioned above. However, it is surprising that such hydrolysis does not occur under the separation conditions employed in the process of the present invention.

The concentration of the activator in the regenerative solution is generally in the range of 0.1 mM to 5M, preferably 1 mM to 5M, more preferably 10 mM to 1M. If the concentration of the activator is too low, the amount of the regenerative solution must be increased in order to activate the chelating resin to a sufficient level. Too large a concentration of the activator is not preferred from an economical viewpoint.

The pH value of a solution containing a plurality of metallic elements to be separated is generally in the range of 1 to 7. It is to be understood that usually, as in the conventional displacement chromatography, all the metallic elements of the solution are not necessarily adsorbed on the chelating resin at one time. The metallic elements which are left in the solution phase, along with the move of the adsorption band, are moved to and adsorbed on the chelating resin at the lower end of the band. On the other hand, at the upper end of the band, the metallic elements are moved from the chelating resin to the solution phase. In this way, the adsorption band is passed down the column.

With respect to the eluting agent, when the separation of rare earth elements is intended, there may be employed metallic ions of Pb (II), Pd(II), Ni(II), Cu(II), V(III), V(IV), Ti(III) and Fe(III), or $H^+$. Of them, $H^+$ is preferred. More preferred are mineral acids such as hydrochloric acid, sulfuric acid and nitric acid, or which the pH value is 3 or less. Most preferred are mineral acids of which the pH value is 1 or less. The higher the acidity of mineral acids, the higher the concentration of rare earth elements separated.

The concentration of the eluting agent in the eluent is generally 0.1 mM to 5M, preferably 1 mM to 5M, more preferably 10 mM to 2M. If the concentration of the eluting agent is too low, the concentration of elements separated into the eluate is unfavorably low. On the other hand, if the concentration of the eluting agent is too high, the rare earth elements tend to form a precipitate by hydrolysis, causing the separation effeciency to be lowered.

The concentration of the metallic elements in the solution containing the metallic elements to be separated is not critical. Generally, the metallic elements are contained at a concentration of 0.1 mM to 1M.

In the process of the present invention, the length of an adsorption band of elements to be separated is not critical. However, it may be 5% to below 100% of the entire length of the adsorbent packed in the column. Then, an eluent is passed through the column for developing the adsorption band. When the length of the adsorption band of elements is less than 5% of the entire length of the adsorbent packed in the column, both productivity and purity of the separated elements are disadvantageously decreased. When the length of an adsorption band of elements to be separated is 100%, purity of the separated elements is disadvantageously decreased whereas productivity is increased (wherein 100% means a state that an adsorption band of elements to be separated is formed on the entire adsorbent in the column).

Usually, the supply of the regenerative solution is effected until the pH value of the effluent becomes the same as that of the regenerative solution.

The supply of the eluent is effected until the metallic elements to be separated are caused to flow out of the column.

The displacement chromatographic process of the present invention may be carried out at a temperature of $-10°$ C. to $200°$ C., preferably $10°$ C. to $120°$ C.

As the solvent or medium to be employed for preparing a regenerative solution, a metallic elements-containing solution and an eluent to be employed in the process of the present invention, water is most generally used. However other kinds of solvents may also be used. Illustrative examples of such other kinds of solvents include acetone, methyl ethyl ketone, dioxane, imidazole, 2-mercaptoethanol, elthylenediamine, thioglycolic acid, methanesulfonic acid, acetonylacetone, sulfamic acid, nitromethane, dimethylacetal, diethyleneglycol, picolinic acid, ethyleneglycol, propyl alcohol, tetrahydrofuran, pyridine, monoethanolamine, 2-aminopyridine, 3-amino-1,2,4-triazole, piperazine, methyl cellosolve ($\beta$-oxyethylmethyl ether), tert-butyl alcohol, dimethylformamide, N-methylformamide, acetonitrile, acetylacetone, urea, oxine, and the like. Furthermore, a stabilizing agent or a complexing agent such as citric acid, or malic acid may be employed.

The process of the present invention is highly useful because by performing the process, it is possible to separate metallic elements, even rare earth elements, separation of which is usually very difficult because of the great physical and chemical similarities therebetween, into individual species not only in a high state of purity, for example 99.9% or more, but also in a high state of concentration.

The present invention will now be illustrated in more detail by the following Examples that should not be construed as limiting the scope of the invention.

In the following Examples, the maximum purity, the recovery and the degree of conversion are defined as follows:

(1) The maximum purity is expressed in terms of mole % of the element contained in a fraction exhibiting the highest purity.

The measurement of the purity was effected by X-ray fluorometry. However, with respect to the fraction which was found to have a purity exceeding 99% by X-ray fluorometry, such fraction was further subjected to an emission spectroscopic analysis by using ICP (an abbreviation of inductively coupled plasma) as the light source. In this case, as the spectrometer, use was made of JY-48 (a spectrometer manufactured and sold by Jobin Yuon, France). With respect to the emission spectroscopic analysis using ICP, reference is made to Shin Jikken Kagaku Koza, Vol.9 (Bunseki Kagaku II), pp208 to 211.

(2) The recovery is expressed in terms of percentage of the total of the amounts of an element contained in fractions each exhibiting a purity higher than 90%, relative to the total amount of said element supplied.

(3) With respect to Adsorbents A, B, C and D, the degree of conversion is obtained as follows:

(i) Adsorbent A $$\text{Conversion (\%)} = \frac{\text{(number of moles of newly incorporated carboxylic acid groups)/2}}{\text{number of moles of chloromethylstyrene incorporated in unit weight of the copolymer}} \times 100$$

(ii) Adsorbent B $$\text{Conversion (\%)} = \frac{\text{(number of moles of newly incorporated carboxylic acid groups)/4}}{\text{number of moles of 1,2-dibromoethyl group incorporated in unit weight of the copolymer}} \times 100$$

(iii) Adsorbent C $$\text{Conversion (\%)} = \frac{\text{(number of moles of newly incorporated carboxylic acid groups)/4}}{\text{number of moles of p-(diaminoethylaminoethyl)styrene incorporated in unit weight of the copolymer}} \times 100$$

(iv) Adsorbent D $$\text{Conversion (\%)} = \frac{\text{(number of moles of newly incorporated carboxylic acid groups)/4}}{\text{number of moles of chloromethyl group incorporated in unit weight of the copolymer}} \times 100$$

With respect to adsorbents A to D, the number of moles of newly incorporated carboxylic acid groups are determined as follows:

After completion of the reaction [in the case of Adsorbent A, the reaction between a chloromethylstyrene-divinylbenzene copolymer and ethyl iminodiacetate; in the case of Adsorbent B, the reaction between (1,2-dibromoethyl)styrenedivinylbenzene copolymer and ethyl iminodiacetate; in the case of Adsorbent C, the reaction between p-(diaminoethylaminoethyl)styrene-divinylbenzene copolymer and ethyl chloroacetate; and in the case of Adsorbent D, the reaction between chloromethylstyrene-divinylbenzene copolymer and diethylenetriamine followed by reaction with ethyl chloroacetate], the reaction product is washed with a solent to remove the materials remaining unreacted, and the functional group of each of the adsorbents is subjected to titration.

EXAMPLE 1

To a crosslinked copolymer of chloromethylstyrene-divinylbenzene (weight ratio of chloromethylstyrene to divinylbenzene: 80/20) was added ethyl iminodiacetate in an amount two times the molar amount of chloromethyl groups of the crosslinked copolymer of chloromethylstyrene-divinylbenzene, and reaction was allowed to proceed at $120°$ C. for 24 hours. The obtained solid product was filtered off using a glass filter and washed with acetone. Thus, there was obtained a granular iminodiacetic acid type chelating resin having a particle diameter of 74 to 147$\mu$ [100 to 200 mesh (Tyler)] (hereinafter referred to as "Adsorbent A"). The degree of coversion was 70%. The obtained chelating resin was packed in a glass-made column equipped with a stopcock for an outlet at the bottom thereof and a jacket and having an inside diameter of 10 mm and a length of 1000 mm. Then the temperature of the whole column was maintained at 50° C., and to the column at its top was supplied an aqueous ammonia having a pH value of 9.0, with the outlet opened by switching the stopcock. The supply of the aqueous ammonia was continued until the pH value of the solution flowing out of the outlet of the column reached 9.0. Thus, the chelating resin was equilibrated with the solution. Then 150 ml of an aqueous solution containing 15 mM each of lanthanum (III) chloride and neodymium (III) chloride and adjusted, by an aqueous hydrogen chloride solution, to have a pH value of 4.0 was supplied to the top of the column at a rate of 3.5 ml/min. Subsequently, a 0.1M aqueous hydrogen chloride solution was fed to the top of the column at a rate of 3.5 ml/min. It took 2 hours for the rear portion of the adsorption band to flow out of the column. During the supply of the 0.1M aqueous hydrogen chloride solution, the rear boundary of the adsorption band which was visible due to the purple neodymium ions present in the rear portion of the band was kept clear. The eluate from the bottom of the column was collected in 5-ml fractions. The concentration of the rare earth elements in each fraction was determined using X-ray fluorescent spectrometer VXQ-150 (an apparatus manufactured and sold by Shimadzu Corporation, Japan).

The concentration of the rare earth element in each fraction exclusive of the fractions corresponding to both the front and rear boundary portions of the adsorption band was about 25 mM. The maximum purity with respect to lanthanum was more than 95% and that with respect to neodymium was also more than 95%. The recovery of each of lanthanum and neodymium was 90%.

EXAMPLES 2 TO 4

Substantially the same procedures as in Example 1 were repeated except that, instead of an aqueous solution containing 15 mM each of lanthanum (III) chloride and neodymium (III) chloride used in Example 1, an aqueous solution containing 15 mM each of praseodymium (III) chloride and neodynium (III) chloride, an aqueous solution containing 15 mM each of neodymium (III) chloride and gadolinium (III) chloride and an aqueous solution containing 15 mM each of yttrium (III) chloride solution and dysprosium (III) chloride were respectively employed in Examples 2 to 4. The results are shown in Table 1.

EXAMPLE 5

To a crosslinked copolymer of (1,2-dibromoethyl)styrene-divinylbenzene [weight ratio of (1,2-dibromoethyl)styrene to divinylbenzene: 80/20] was added ethyl iminodiacetate in an amount four times the molar amount of 1,2-dibromo groups of the crosslinked copolymer of (1,2-dibromoethyl)styrene-divinylbenzene, and reaction was allowed to proceed at 120° C. for 24 hours. The obtained solid product was filtered off using a glass filter and washed with acetone. Thus, there was obtained a granular E.D.T.A type chelating resin having a particle diameter of 74 to 147μ [100 to 200 mesh (Tyler)] (hereinafter referred to as "Adsorbent B"). The degree of conversion was 60%. The obtained chelating resin was packed in a glass-made column equipped with a stopcock for an outlet at the bottom thereof and a jacket and having an inside diameter of 10 mm and a length of 1000 mm. Then the temperature of the whole column was maintained at 50° C., and to the column at its top was supplied an aqueous ammonia having a pH value of 9.0, with the outlet opened by switching the stopcock. The supply of the aqueous ammonia was continued until the pH value of the solution flowing out of the outlet of the column reached 9.0. Thus the chelating resin was equilibrated with the solution. Then 150 ml of an aqueous solution containing 10 mM each of lanthanum (III) chloride and neodymium (III) chloride and adjusted, by an aqueous hydrogen chloride solution, to have a pH value of 4.0 was supplied to the top of the column at a rate of 3.5 ml/min. Subsequently, a 0.1M aqueous hydrogen chloride solution was fed to the top of the column at a rate of 3.5 ml/min. The eluate from the bottom of the column were collected in 5-ml fractions. The concentration of the rare earth elements in each fraction was determined using X-ray fluorescent spectrometer VXQ-150 (an apparatus manufactured and sold by Shimadzu Corporation, Japan). The results are shown in Table 1.

EXAMPLE 6

Substantially the same procedures as in Example 5 were repeated except that an aqueous solution containing 6 mM each of praseodymium (III) chloride and neodymium (III) chloride was used instead of an aqueous solution containing 10 mM each of lanthanum (III) chloride and neodymium (III) chloride. The results are shown in Table 1.

EXAMPLE 7

Substantially the same procedures as in Example 5 were repeated except that an aqueous solution containing 50 mM each of praseodymium (III) chloride and neodymium (III) chloride and a 0.45M aqueous hydrogen chloride solution were respectively used instead of an aqueous solution containing 10 mM each of lanthanum (III) chloride and neodymium (III) chloride and a 0.1M aqueous hydrogen chloride solution. The results are shown in Table 1.

EXAMPLE 8

Substantially the same procedures as in Example 5 were repeated except that an aqueous solution containing 10 mM each of yttrium (III) chloride and dysprosium (III) chloride was used instead of an aqueous solution containing 10 mM each of lanthanum (III) chloride and neodymium (III) chloride. The results are shown in Table 1.

EXAMPLE 9

Substantially the same procedures as in Example 5 were repeated except that an aqueous solution containing 150 mM each of yttrium (III) chloride and dysprosium (III) chloride and a 1.2M aqueous hydrogen chloride solution were respectively used instead of an aqueous solution containing 10 mM each of lanthanum (III) chloride and neodymium (III) chloride and a 0.1M aqueous hydrogen chloride solution. The results are shown in Table 1.

EXAMPLE 10

Substantially the same procedures as in Example 5 were repeated except that an aqueous solution containing 20 mM each of yttrium (III) chloride and dysprosium (III) chloride and a 0.1M aqueous sulfuric acid solution were respectively used instead of an aqueous solution cotaining 10 mM each of lanthanum (III) chloride and neodymium (III) chloride and a 0.1M aqueous hydrogen chloride solution. The results are shown in Table 1.

EXAMPLE 11

To a crosslinked copolymer of p-(diaminoethylaminoethyl)styrene-divinylbenzene [weight ratio of p-(diaminoethylaminoethyl)styrene to divinylbenzene: 80/20] was added ethyl chloroacetate in an amount 8 times the molar amount of p-(diaminoethylaminoethyl)styrene units of the crosslinked copolymer of p-(diaminoethylaminoethyl)styrene-divinylbenzene, and reaction was allowed to proceed at 90° C. for 24 hours. The obtained solid product was filtered off using a glass filter and washed with acetone. Thus, there was obtained a granular chelating resin having a particle diameter of 37 to 147μ [100 to 400 mesh (Tyler)] (hereinafter referred to as "Adsorbent C"). The degree of conversion was 54%. The obtained resin was packed in a glass-made column equipped with a stopcock for an outlet at the bottom thereof and a jacket and having an inside diameter of 10 mm and a length of 1000 mm. Then the temperature of the whole column was maintained at 50° C., and to the column at its top was supplied an aqueous ammonia having a pH value of 9.0, with the outlet opened by switching the stopcock. The supply of the aqueous ammonia was continued until the pH value of the solution flowing out of the outlet of the column reached 9.0. Thus the chelating resin was equilibrated with the solution. Then 150 ml of an aqueous solution containing 10 mM each of lanthanum (III) chloride and neodymium (III) chloride and adjusted, by an aqueous hydrogen chloride solution, to have a pH value of 4.0 was supplied to the top of the column at a rate of 3.5 ml/min. Subsequently, a 0.1M aqueous hydrogen chloride solution was fed to the top of the column at a rate of 3.5 ml/min. The eluate from the bottom of the column was collected in 5-ml fractions. The concentration of the rare earth elements in each fraction was determined using X-ray fluorescent spectrometer VXQ-150 (an apparatus manufactured and sold by Shimadzu Corporation, Japan). The results are shown in Table 1.

EXAMPLE 12

Substantially the same procedures as in Example 11 were repeated except that an aqueous solution containing 50 mM each of praseodymium (III) chloride and neodymium (III) chloride and a 0.45M aqueous hydrogen chloride solution were respectively used instead of an aqueous solution containing 10 mM each of lanthanum (III) chloride and neodymium (III) chloride and a 0.1M aqueous hydrogen chloride solution. The results are shown in Table 1.

EXAMPLE 13

Substantially the same procedures as in Example 11 were repeated except that an aqueous solution containing 130 mM each of praseodymium (III) chloride and neodymium (III) chloride, a 1.2M aqueous hydrogen chloride solution and an aqueous NaOH solution having a pH value of 11.5 were respectively used instead of an aqueous solution containing 10 mM each of lanthanum (III) chloride and neodymium (III) chloride, a 0.1M aqueous hydrogen chloride solution and an aqueous ammonia having a pH value of 9. The results are shown in Table 1.

EXAMPLE 14

Substantially the same procedures as in Example 11 were repeated except that an aqueous solution containing 10 mM each of praseodymium (III) chloride and neodymium (III) chloride, and a 0.5M aqueous ammonium chloride soltuion adjusted, by addition of ammonia, to have a pH value of 6 were respectively used instead of an aqueous solution containing 10 mM each of lanthanum (III) chloride and neodymium (III) chloride and an aqueous ammonia having a pH value of 9. The results are shown in Table 1.

EXAMPLE 15

Substantially the same procedures as in Example 11 were repeated except that an aqueous solution containing 15 mM each of yttrium (III) chloride and dysprosium (III) chloride was used instead of an aqueous solution containing 10 mM each of lanthanum (III) chloride and neodymium (III) chloride. The results are shown in Table 1.

EXAMPLE 16

To a crosslinked copolymer of chloromethylstyrene-divinylbenzene (weight ratio of chloromethylstyrene to divinylbenzene: 80/20) was added diethylenetriamine in an amount 2 times the molar amount of chloromethyl groups of the crosslinked copolymer of chloromethylstyrene-divinylbenzene and reaction was allowed to proceed at room temperature for 4 hours. The obtained solid product was filtered off using a glass filter and washed with acetone to obtain an intermediate. To the obtained intermediate was added ethyl chloroacetate in an amount 8 times the molar amount of diethylenetriamine consumed by the above reaction and reaction was allowed to proceed at 90° C. for 24 hours. The obtained solid product was filtered off using a glass filter and washed with acetone to obtain a chelating resin having a particle diameter of 37 to 147μ [100 to 400 mesh (Tyler)] (hereinafter referred to as "Adsorbent D"). The degree of conversion was 50%. The obtained chelating resin was packed in a glass-made column equipped with a stopcock for an outlet at the bottom thereof and a jacket and having an inside diameter of 10 mm and a length of 1000 mm. Then the temperature of the whole column was maintained at 50° C., and to the column at its top was supplied an aqueous ammonia having a pH value of 9.0, with the outlet opened by switching the stopcock. The supply of the aqueous ammonia was continued until the pH value of the solution flowing out of the outlet of the column reached 9.0. Thus the chelating resin was equilibrated with the solution. Then 150 ml of an aqueous solution containing 15 mM each of lanthanum (III) chloride and neodymium (III) chloride and adjusted, by an aqueous hydrogen chloride solution, to have a pH value of 4.0 was supplied to the top of the column at a rate of 3.5 ml/min. Subsequently, a 0.1M aqueous hydrogen chloride solution was fed to the top of the column at a rate of 3.5 ml/min. The eluate from the bottom of the column was collected in 5-ml fractions. The concentration of the rare earth elements in each fraction was determined using X-ray fluorescent spectrometer VXQ-150 (an apparatus manufactured and sold by Shimadzu Corporation, Japan). The results are shown in Table 1.

EXAMPLE 17

Substantially the same procedures as in Example 16 were repeated except that an aqueous solution containing 10 mM each of praseodymium (III) chloride and neodymium (III) chloride was used instead of an aqueous solution containing 15 mM each of lanthanum (III) chloride and neodymium (III) chloride. The results are shown in Table 1.

EXAMPLE 18

Substantially the same procedures as in Example 16 were repeated except that an aqueous solution containing 10 mM each of neodymium (III) chloride and gadolinium (III) chloride was used instead of an aqueous solution containing 15 mM each of lanthanum (III) chloride and neodymium (III) chloride. The results are shown in Table 1.

EXAMPLE 19

Substantially the same procedures as in Example 16 were repeated except that an aqueous solution containing 10 mM each of yttrium (III) chloride and dysprosium (III) chloride was used instead of an aqueous solution containing 15 mM each of lanthanum (III) chloride and neodymium (III) chloride. The results are shown in Table 1.

EXAMPLE 20

Substantially the same procedures as in Example 16 were repeated except that an aqueous solution containing 15 mM each of yttrium (III) chloride and dysprosium (III) chloride, a 0.1M aqueous sulfuric acid solution and an aqueous NaOH solution having a pH value of 11.5 were used instead of an aqueous solution containing 15 mM each of lanthanum (III) chloride and neodymium (III) chloride, a 0.1M aqueous hydrogen chloride solution and an aqueous ammonia having a pH value of 9, respectively. The results are shown in Table 1.

COMPARATIVE EXAMPLE

Separation of metallic elements by displacement chromatography was effected in substantially the same manner as in Example 1, except that Dowex 1×8 (a gel type strongly basic ion exchange resin manufactured and sold by Dow Chemical, U.S.A.; hereinafter referred to as "Adsorbent E") was used as a resin to be packed in the column.

The results obtained are shown in Table 1.

TABLE 1

| Example No. | Adsorbent | Regenerative solution containing an activator (pH) | Eluent (concentration, M) | Solution containing elements to be separated | | After Separation | | |
|---|---|---|---|---|---|---|---|---|
| | | | | Element species (molar ratio) | Concentration* (mM) | Concentration* (mM) | Element species of front band / rear band | Maximum purity (mole %) | Recovery (%) |

| Example No. | Adsorbent | Regenerative solution (pH) | Eluent (conc., M) | Element species (molar ratio) | Conc.* (mM) | Conc.* (mM) | Element species | Maximum purity (mole %) | Recovery (%) |
|---|---|---|---|---|---|---|---|---|---|
| 1 | A | Aqueous ammonia (9) | Aqueous HCl solution (0.1) | La/Nd (1:1) | 30 | 25 | La | 95 | 90 |
| | | | | | | | Nd | 95 | 90 |
| 2 | A | Aqueous ammonia (9) | Aqueous HCl solution (0.1) | Pr/Nd (1:1) | 30 | 21 | Pr | 72 | 0 |
| | | | | | | | Nd | 55 | 0 |
| 3 | A | Aqueous ammonia (9) | Aqueous HCl solution (0.1) | Nd/Gd (1:1) | 30 | 19 | Nd | 60 | 0 |
| | | | | | | | Gd | 65 | 0 |
| 4 | A | Aqueous ammonia (9) | Aqueous HCl solution (0.1) | Y/Dy (1:1) | 30 | 18 | Y | 92 | 15 |
| | | | | | | | Dy | 89 | 7 |
| 5 | B | Aqueous ammonia (9) | Aqueous HCl solution (0.1) | La/Nd (1:1) | 20 | 23 | La | 95 | 95 |
| | | | | | | | Nd | 95 | 95 |
| 6 | B | Aqueous ammonia (9) | Aqueous HCl solution (0.1) | Pr/Nd (1:1) | 12 | 19 | Pr | 95 | 92 |
| | | | | | | | Nd | 95 | 90 |
| 7 | B | Aqueous ammonia (9) | Aqueous HCl solution (0.45) | Pr/Nd (1:1) | 100 | 90 | Pr | 95 | 91 |
| | | | | | | | Nd | 95 | 93 |
| 8 | B | Aqueous ammonia (9) | Aqueous HCl solution (0.1) | Y/Dy (1:1) | 20 | 19 | Y | 99.99 | 92 |
| | | | | | | | Dy | 99.99 | 95 |
| 9 | B | Aqueous ammonia | Aqueous HCl solution (1.2) | Y/Dy (1:1) | 300 | 255 | Y | 99.92 | 75 |
| | | | | | | | Dy | 99.81 | 70 |
| 10 | B | Aqueous ammonia | Aqueous H$_2$SO$_4$ solution (0.1) | Y/Dy (1:1) | 20 | 35 | Y | 99.99 | 91 |
| | | | | | | | Dy | 99.99 | 93 |
| 11 | C | Aqueous ammonia | Aqueous HCl solution (0.1) | La/Nd (1:1) | 20 | 24 | La | 95 | 91 |
| | | | | | | | Nd | 95 | 93 |
| 12 | C | Aqueous ammonia | Aqueous HCl solution (0.45) | Pr/Nd (1:1) | 100 | 90 | Pr | 95 | 89 |
| | | | | | | | Nd | 95 | 91 |
| 13 | C | Aqueous NaOH solution (11.5) | Aqueous HCl solution (1.2) | Pr/Nd (1:1) | 260 | 250 | Pr | 85 | 83 |
| | | | | | | | Nd | 86 | 74 |
| 14 | C | 0.5M aqueous ammonium chloride solution containing ammonia (6) | Aqueous HCl solution (0.1) | Pr/Nd (1:1) | 30 | 18 | Pr | 95 | 85 |
| | | | | | | | Nd | 95 | 86 |
| 15 | C | Aqueous ammonia (9) | Aqueous HCl solution (0.1) | Y/Dy (1:1) | 20 | 25 | Y | 99.99 | 92 |
| | | | | | | | Dy | 99.99 | 91 |
| 16 | D | Aqueous ammonia (9) | Aqueous HCl solution (0.1) | La/Nd (1:1) | 30 | 25 | La | 95 | 89 |
| | | | | | | | Nd | 95 | 88 |
| 17 | D | Aqueous ammonia (9) | Aqueous HCl solution (0.1) | Pr/Nd (1:1) | 20 | 21 | Pr | 92 | 85 |
| | | | | | | | Nd | 95 | 81 |
| 18 | D | Aqueous ammonia (9) | Aqueous HCl solution (0.1) | Nd/Gd (1:1) | 20 | 20 | Nd | 90 | 86 |
| | | | | | | | Gd | 89 | 88 |
| 19 | D | Aqueous | Aqueous HCl | | 20 | 20 | Y | 99.91 | 88 |

TABLE 1-continued

| Example No. | Adsorbent | Regenerative solution containing an activator (pH) | Eluent (concentration, M) | Solution containing elements to be separated | | After Separation | | | |
| | | | | Element species (molar ratio) | Concentration* (mM) | Concentration* (mM) | Element species of front band | Maximum purity (mole %) | Recovery (%) |
| | | | | | | | Element species of rear band | Maximum purity (mole %) | Recovery (%) |
| --- | --- | --- | --- | --- | --- | --- | --- | --- | --- |
| 20 | D | ammonia (9) Aqueous NaOH solution (11.5) | solution (0.1) Aqueous H₂SO₄ solution (0.1) | (1:1) Y/Dy (1:1) | 30 | 33 | Dy Y Dy | 99.88 99.92 99.31 | 85 87 84 |
| Comparative Example | E | Aqueous ammonia (9) | Aqueous HCl solution (0.1) | Nd/Pr (1:1) | 30 | on average 21 | Elements could not be separated at all. | | |

*The concentration means the sum of concentration of two elements.

EXAMPLE 21

Adsorbent C was packed in the same column as that used in Example 1. To the column at its top was supplied an aqueous ammonia having a pH value of 9.0, with the outlet opened by switching the stopcock. The supply of the aqueous ammonia was continued until the pH value of the solution flowing out of the outlet of the column reached 9.0. Thus the chelating resin was equilibrated with the solution. Then, 150 ml of an aqueous solution containing 10 mM each of lanthanum (III) chloride, praseodymium (III) chloride and neodymium (III) chloride and adjusted to have a pH value of 4.0 by addition of an aqueous hydrogen chloride solution was supplied to the top of the column at a rate of 3.5 ml/min. Subsequently, a 0.1M aqueous hydrogen chloride solution was fed to the top of the column at a rate of 3.5 ml/min. The eluate from the bottom of the column were collected in 3-ml fractions. The concentration of the rare earth elements in each fraction was determined using X-ray fluorescent spectrometer VXQ-150 (an apparatus manufactured and sold by Shimadzu Corporation, Japan). As a result, it was found that lanthanum, praseodymium and neodymium were almost completely separated in this sequence. The recoveries of lanthanum, praseodymium and neodymium were 88%, 85% and 86%, respectively.

What is claimed is:

1. A process for separating and purifying metallic elements by displacement chromatography, which comprises the steps of:
(1) in either order,
(a) packing a column with a resin; and
(b) treating the resin with a regenerative solution containing an activator,
to obtain a column of an activated resin;
said resin being one having a chelating group of a structure derived by removing a hydrogen atom from a chelating compound of the formula:

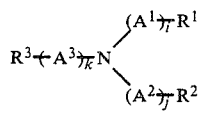  (I)

in which $R^1$, $R^2$ and $R^3$ each independently represent a hydrogen atom or a group of the formula:

in which $R^5$ represents a hydrogen atom, a metal atom or a hydrocarbon residue having 1 to 4 carbon atoms;

$A^1$, $A^2$ and $A^3$ each independently represent a group of the formula:

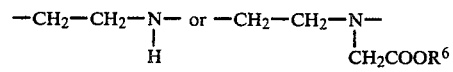

in which $R^6$ has the same meaning as that of $R^5$; and i, j and k each independently are an integer of 0 to 3, exclusive of the case of all of i, j and k being concurrently 0;

(2) passing through the column of the activated resin a solution containing a plurality of metallic elements to be separated to adsorb the elements on the activated resin, thereby forming an adsorption band of the metallic elements in the column packed with the activated resin;
(3) passing an eluent through the column of the resin having the adsorption band of the metallic elements to form the individual metallic elements into bands;
(4) further passing an eluent through the column, causing the bands of the individual metallic elements to pass down the column; and
(5) collecting successive portions of the resultant eluate.

2. A process according to claim 1, wherein the chelating group is a group of the formula:

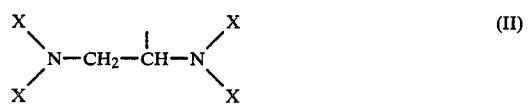  (II)

in which X represents a hydrogen atom or a group of the formula:

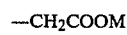

in which M represents a metal atom or a hydrogen atom.

3. A process according to claim 1, wherein the chelating group is a group of the formula:

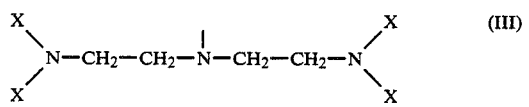  (III)

in which X represents a hydrogen atom or a group of the formula:

—CH₂COOM in which M represents a metal atom or a hydrogen atom.

4. A process according to claim 1, wherein the chelating group is a group of the formula:

$$\begin{array}{c}X\\ \diagdown\\ X\diagup\end{array}N-CH_2-CH_2-N-CH_2-CH_2-N\begin{array}{c}\diagup\\ \diagdown X\end{array} \quad (IV)$$
$$\phantom{XXXXXXXXXXX}|\\ \phantom{XXXXXXXXXXX}X$$

in which X represents a hydrogen atom or a group of the formula:

—CH₂COOM in which M represents a metal atom or a hydrogen atom.

5. A process according to claim 1, wherein the metallic elements to be separated are elements of Group III and Group IV of the long period periodic table.

6. A process according to claim 5, wherein said elements of Group III and Group IV are rare earth elements, aluminum, gallium, zirconium and hafnium.

7. A process according to claim 5, wherein said elements of Group III and Group IV are rare earth elements.

8. A process according to claim 7, wherein the rare earth elements are yttrium and dysprosium.

9. A process according to claim 4, wherein the regenerative solution is an aqueous solution containing an activator and having a pH value of 4 or more and the eluent is an aqueous solution containing an eluting agent and having a pH value of 3 or less.

10. A process according to claim 9, wherein the activator is an ammonium salt, a sodium salt or a mixture thereof.

11. A process according to claim 9, wherein the eluting agent is at least one member selected from the group consisting of hydrochloric acid, sulfuric acid and nitric acid.

12. A process according to claim 10, wherein the eluting agent is at least one member selected from the group consisting of hydrochloric acid, sulfuric acid and nitric acid.

13. A process according to claim 5, wherein the metallic elements to be separated are selected from the group consisting of praseodymium, neodymium, yttrium, dysprosium, lanthanide and gadolinium.

14. A process according to claim 3, wherein the metallic elements to be separated are a mixture of praseodymium and neodymium; yttrium and dysprosium; lanthanide and neodymium; praseodymium and neodymium; or neodymium and gadolinium.

15. A process according to claim 1, wherein said resin has a copper ion adsorbing capacity of 0.5 millimole or more per gram of dried resin.

* * * * *